(12) United States Patent
Graves et al.

(10) Patent No.: US 6,855,947 B2
(45) Date of Patent: Feb. 15, 2005

(54) OPTICAL PRECIPITATION SENSOR FOR MONITORING THE ACCUMULATION OF PRECIPITATION UPON AUTOMOTIVE GLASS

(75) Inventors: Danny Graves, Springfield, TN (US); Jaroslav Purma, Karvina (CZ); Jiri Kocarek, Jablonec nad Nisou (CZ); Jaromir Lan, Ruprechticka (CZ)

(73) Assignee: The Gates Corporation, Denver, CO (US)

( * ) Notice: Subject to any disclaimer, the term of this patent is extended or adjusted under 35 U.S.C. 154(b) by 10 days.

(21) Appl. No.: 09/909,453

(22) Filed: Jul. 19, 2001

(65) Prior Publication Data

US 2002/0033459 A1 Mar. 21, 2002

Related U.S. Application Data

(60) Provisional application No. 60/219,170, filed on Jul. 19, 2000.

(51) Int. Cl.[7] .............................................. G01N 15/06
(52) U.S. Cl. ................................. 250/573; 250/227.25
(58) Field of Search ............................... 250/573–575, 250/227.25; 356/335–343; 318/483; 340/602–604

(56) References Cited

U.S. PATENT DOCUMENTS

| | | | |
|---|---|---|---|
| 4,355,271 A | 10/1982 | Noack | 318/480 |
| 4,620,141 A | 10/1986 | McCumber et al. | 318/483 |
| 4,676,638 A * | 6/1987 | Yasuda | 356/239.8 |
| 4,798,956 A | 1/1989 | Hochstein | 250/341 |
| 4,916,374 A | 4/1990 | Schierbeek et al. | 318/483 |
| 4,960,996 A | 10/1990 | Hochstein | 250/349 |
| 4,973,844 A | 11/1990 | O'Farrell et al. | 250/341 |
| 5,059,877 A | 10/1991 | Teder | 318/444 |
| 5,661,303 A | 8/1997 | Teder | 250/341.8 |
| 5,811,793 A * | 9/1998 | Pientka | 250/227.25 |
| 5,898,183 A | 4/1999 | Teder | 250/574 |
| 6,285,037 B1 * | 9/2001 | Koyama et al. | 250/574 |

FOREIGN PATENT DOCUMENTS

CZ    285 291    4/1999    ............. B60S/1/08

* cited by examiner

Primary Examiner—Thanh X. Luu
(74) Attorney, Agent, or Firm—S. G. Austin, Esq.; C. H. Castleman, Esq.; J. A. Thurnau, Esq.

(57) ABSTRACT

The invention is a precipitation sensor adapted to detect water upon an automotive glass and a method for its use. The precipitation sensor includes an optical emitter and a first mirror surface in optical communication with the optical emitter. The first mirror surface is adapted to reflect and collimate light emission from the optical emitter. The precipitation sensor also includes an optical receiver and a second mirror surface in optical communication with the optical receiver. The second mirror surface is adapted to focus collimated light upon the optical receiver. The precipitation sensor further includes an intermediate reflector in optical communication with the first mirror surface and with the second mirror surface.

12 Claims, 4 Drawing Sheets

OPTICAL PRECIPITATION SENSOR FOR MONITORING THE ACCUMULATION OF PRECIPITATION UPON AUTOMOTIVE GLASS

This application claims priority to U.S. Provisional Patent Application Ser. No. 60/219,170, filed Jul. 19, 2000 and entitled OPTICAL PRECIPITATION SENSOR. The subject matter of this application is incorporated herein by this reference.

The U.S. Pat. No. 4,798,956 to Hochstein employed two methods toward overcoming the ambient light problem. For the first method, the receiver was placed at the bottom of a black tube to limit the number of directions from which ambient light could successfully reach the receiver. The use of infrared emitters was central to the second method employed. The '956 patent stated that infrared emitters was used to compensate for ambient light. It indicated that commercially available infrared eminers emitted peak energy at 940 nm, in contrast to solar radiant energy peaking at approximately 500 mn. A filter was then placed in the tube between the opening of the tube and the receiver which passed the infrared light but rejected light of wavelengths shorter than infrared, including the peak solar wavelength of 500 nm.

BACKGROUND OF THE INVENTION

1. Field of the Invention

This invention relates generally to precipitation sensors associated with monitoring the accumulation of precipitation upon window glass. More particularly, this invention relates to optical precipitation sensors used in automotive applications. Specifically, this invention relates to the optics used in automotive optical precipitation sensors and a method for their use.

2. Description of the Prior Art

It is desirable to free the driver, operating an automobile, from the distractions of manually performing certain functions associated with the operation of the automobile. Comfort and safety can be both served by automating these functions. Operation of the wipers for the windshield or other window glass of an automobile, is a function that has been automated.

Automating the operation of these wipers requires sensing the presence of water, or precipitation, upon the outer surfaces of the window glass. When water is sensed, a signal is generated, electronic circuitry processes the signal, and the wipers are automatically deployed to clear the water from the window glass surface. Several approaches have been taken toward this sensing of water on window glass. These have included sensing a change in conductivity or capacitance, at a sampling point upon the outer surface, when moisture is present. These have included acoustic effects produced by raindrops hitting the surface of the automobile (e.g. rain landing upon the window glass or some other portion of the vehicle). These approaches have also included various optical techniques.

Optical sensors operate on the principle that a light beam is diffused or deflected from its normal path by the presence of water on the outer surface of the window. The systems that use optical sensors have the distinct advantage that they are sensing the same or similar phenomenon, which gives rise to the need for wiper operation, that being the disruption of the light transmissibility of the window glass caused by water residing on the outer surface.

Generally, a beam of light, in the infrared or near infrared ranges, is emitted into the window glass, from inside of the automobile, and at an angle giving rise to total reflection at the outer surface. A photoelectric device, such as a photodiode or a phototransistor, then receives the reflected light and produces a representative electrical signal. The light received at the photoelectric device has certain characteristics when the outer surface is dry. The characteristics are altered when water is present on the outer surface, at the point where the light beam comes into contact with the outer surface. Since water has a refractive index close to that of glass, its presence causes a substantial portion of the light, which would otherwise be reflected to the receiver, to dissipate. This change in characteristics results in commensurate change in the electrical signal produced by the photoelectric device. The signal is processed by electronic circuitry to control the operation of the wipers.

A recent approach disclosed in U.S. Pat. No. 5,661,303 to Teder, for producing an optical precipitation sensor, includes the use of emission lenses to collimate infrared light emitted from multiple Light Emitting Diodes (LED) and to direct the light upon the outer surface of the window glass at angles giving rise to total reflection. Reception lenses are then used to direct and focus the reflected emitted light upon receivers.

Another recent approach is disclosed in Czech Republic Patent numbered CZ 285,291 B6, to Lan et al., uses a rotational parabolic mirror to collimate and direct near infrared light from multiple LED's upon the outer surface at an angle giving rise to total reflection. The reflected emitted light is then directed and focused upon a receiver by another rotational parabolic mirror.

An issue that arises in connection with the use of optical sensors, for precipitation detection, is desensitization of the photoelectric device of the receiver, by ambient light. Bright ambient light, such as sunlight, impinging upon the photoelectric device of the receiver, causes the device to become relatively insensitive to the emitted light transmitted to the receiver. If enough ambient light is impinging upon the receiver, the signal produced by the receiver may not be adequately different, in response to the presence of water on the outer surface, to be useable by the electronics to reliably control the wipers.

The approach using lenses, of the '303 patent, apparently includes opaque members proximate and lateral to the optical axes of the reception lenses to block a portion of the ambient light reaching the receivers. The '291 patent does not discuss nor depict any means for blocking ambient light from reaching the receiver.

The U.S. Pat. No. 4,798,956 to Hochstein employed two methods toward overcoming the ambient light problem. For the first method, the receiver was placed at the bottom of a black tube to limit the number of directions from which ambient light could successfully reach the receiver. The use of infrared emitters was central to the second method employed. The '956 patent stated that infrared was used to compensate for ambient light. It indicated that commercially available infrared emitters emitted peak energy at 940 nm, in contrast to solar radiant energy peaking at approximately 500 nm. A filter was then placed in the tube between the opening of the tube and the receiver which passed the infrared light but rejected light of wavelengths shorter than infrared, including the peak solar wavelength of 500 nm.

Apparently, none of the approaches disclosed adequately protect the receiver from ambient light to ensure proper sensing of water on an outer surface of a window glass, in all light conditions expected to be encountered by a precipitation sensor.

Additionally, the advent of solar or thermal glass, for automotive applications, creates new challenges for the optical precipitation sensor designer. Solar glass includes additives to filter infrared and near infrared light from passing through the glass. Such glass protects the interior of the automobile from heating and other deleterious effects of this wavelength of light. However, it also substantially inhibits the infrared light of the emitter from reaching the receiver. It has been found that at least some infrared optical precipitation sensors are unusable in conjunction with such glass. The problem of ambient light rejection, evident in prior art designs, is exacerbated when the use of infrared emitters is no longer a viable option.

Accordingly, there remains the need for an optical precipitation sensor exhibiting improved ambient light rejection particularly when used in conjunction with solar or thermal glass.

SUMMARY OF THE INVENTION

The present invention has as an object the provision of an optical precipitation sensor with improved ambient light rejection.

The present invention has the further object of allowing improved operation of an optical precipitation sensor in the least favorable light conditions expected to be encountered by an automotive precipitation sensor.

The present invention has the further object of allowing the effective use of an optical precipitation sensor in conjunction with solar or thermal automotive glass.

To achieve the foregoing and other objects in accordance with the purposes of the present invention, as embodied and broadly described herein, an optical precipitation sensor and method is disclosed herein. The invention is a precipitation sensor adapted to detect water upon an automotive glass and a method for its use. The precipitation sensor includes an optical emitter and a first mirror surface in optical communication with the optical emitter. The first mirror surface is adapted to reflect and collimate light emission from the optical emitter. The precipitation sensor also includes an optical receiver and a second mirror surface in optical communication with the optical receiver. The second mirror surface is adapted to focus collimated light upon the optical receiver. The precipitation sensor further includes an intermediate reflector in optical communication with the first mirror surface and with the second mirror surface.

BRIEF DESCRIPTION OF THE INVENTION

The accompanying drawings, which are incorporated in and form part of the specification in which like numerals designate like parts, illustrate preferred embodiments of the present invention and together with the description, serve to explain the principles of the invention. In the drawings.

DETAILED DESCRIPTION OF THE PREFERRED EMBODIMENTS

Figure 1:
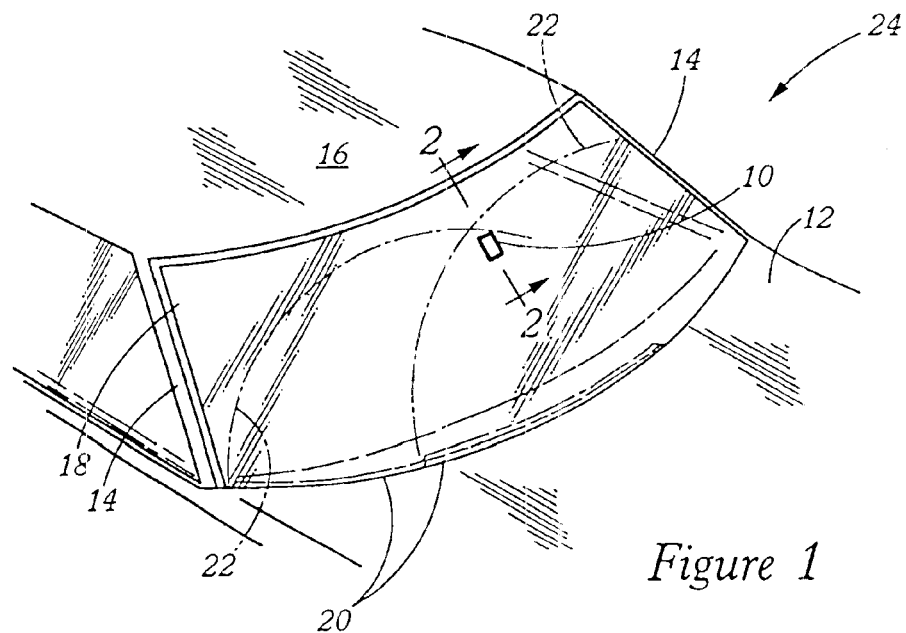
FIG. 1 is a fragmentary perspective depicting an optical precipitation sensor mounted upon a windshield of an automobile.

Referring to FIG. 1, optical precipitation sensor 10 of the instant invention is shown in relation to automobile 24, including an opening defined by, hood 12, side posts 14, roof 16, within which is located windshield 18. Windshield wipers 20 are shown in their rest position with the arcs of their sweep of operation shown by arcs 22. Optical precipitation sensor 10 is depicted in a preferred location within the reach of wipers 20 in operation. While mounting of optical precipitation sensor 10 is depicted upon windshield 18, mounting upon any window glass where sensing of precipitation is desired is contemplated, including rear or side windows, sunroofs, or headlamps.

Figure 2:
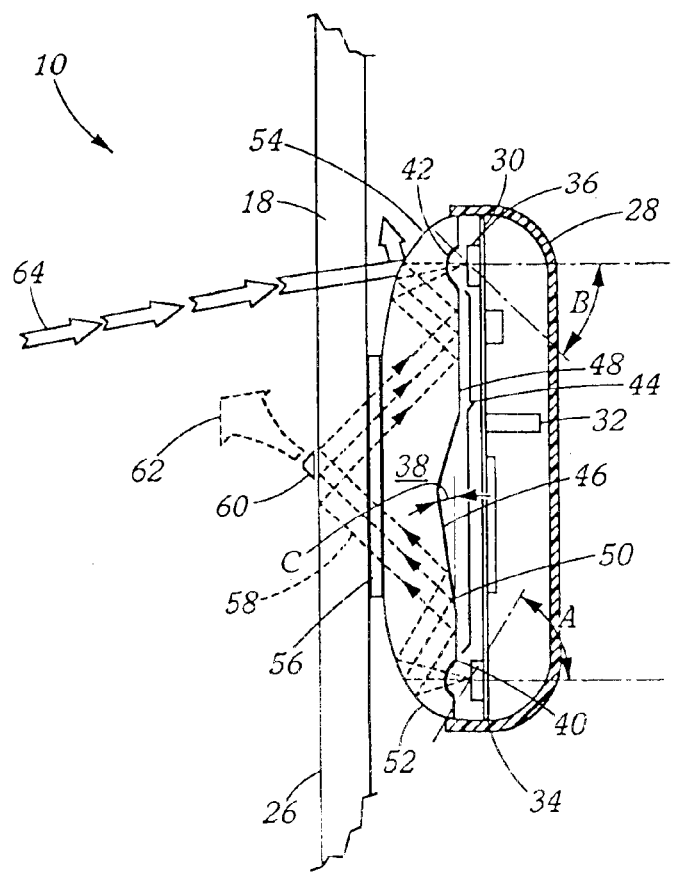
FIG. 2 is a transverse section of the optical precipitation sensor and windshield, taken along line 2—2 of FIG. 1.
Figure 3:
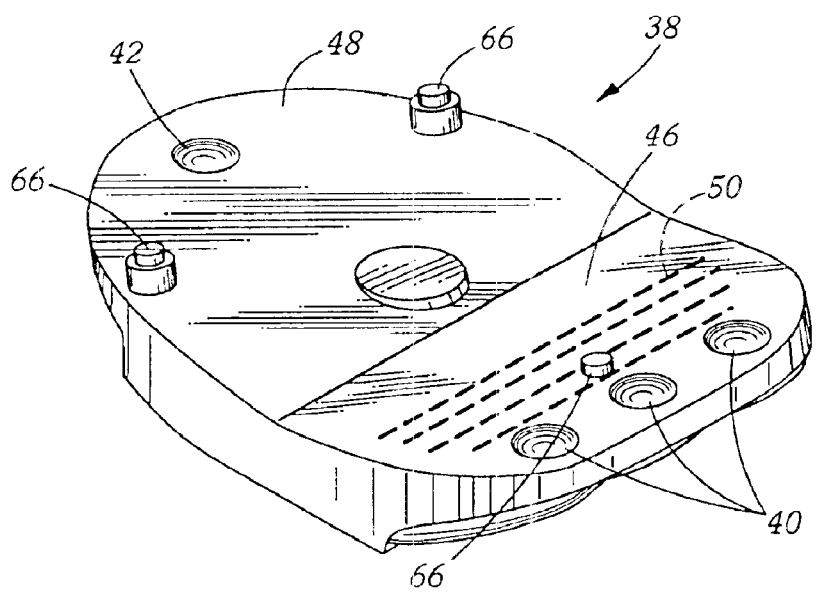
FIG. 3 is a perspective of the glass molding.
Figure 4:
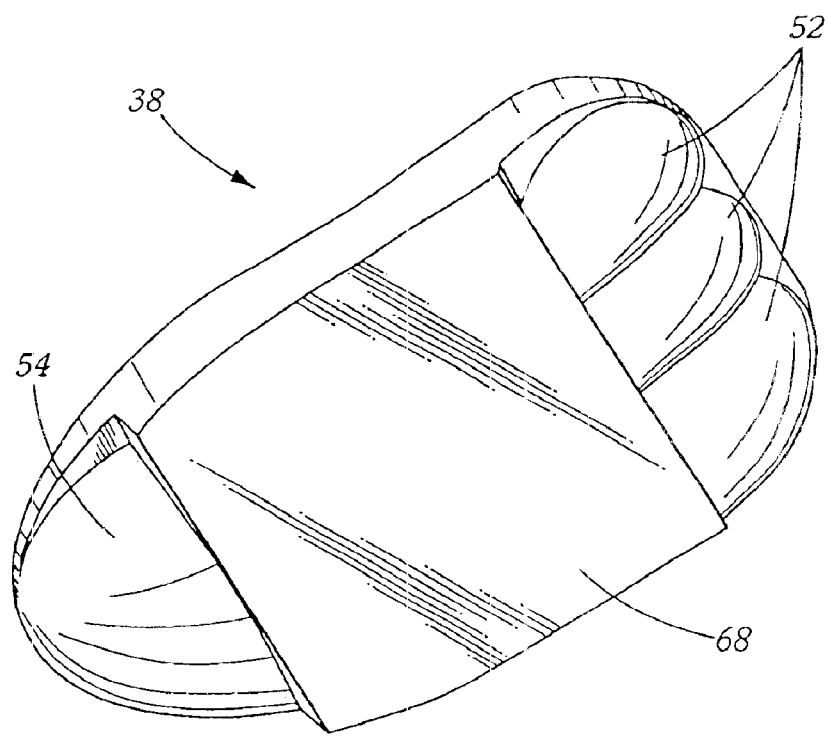
FIG. 4 is a perspective of the glass molding.

Referring to FIGS. 2, 3, and 4 optical precipitation sensor 10 includes housing 28, which contains circuit board 30 and glass molding 38. Circuit board 30 serves as the mounting substrate for all of the electronic circuitry including electronic components 32, emitters 34 and receiver 36. These electronic components 32 process the signals related to emitters 34 and receiver 36 and provide an electrical interface to automobile 24 in a conventional manner known to those of ordinary skill in the art and will not be described herein.

In this preferred embodiment, molding glass 38 is a single piece of glass and includes all optics of optical precipitation sensor 10, other than emitters 34 and receiver 36, and includes emitter optical notches 40, receiver optical notch 42, intermediate reflector 44, first mirror surfaces 52, and second mirror surface 54. Locator posts 66 also form part of glass molding 38, seen in FIG. 3, and mate with holes (not depicted) on circuit board 30 to ensure consistent alignment of emitters 34 with emitter optical notches 40 and of receiver 36 with receiver optical notch 42.

As will be discussed below, the configuration of the instant invention, using second mirror surface 54 to shield receiver 36, very substantially reduces access of ambient light to receiver 36. However, molding glass 38 preferably includes coloring agents to filter out ambient light 64 at wave lengths other than emitted by emitter 34, which further excludes ambient light 64 from accessing receiver 36. The glass composition used in application to clear and tinted windshields 18 is more preferably formulated to transmit the same wavelength of light as is emitted by emitters 34. Such filtering properties of the glass are achieved by adding the following colorants into the glass:

CoO (in the range from 0.01 wt. % to 1.0 wt. %)
CeO2 (in the range from 0.0 wt. % to 6.0 wt. %)
TiO2 (in the range from 0.0 wt. % to 1.0 wt. %)
NiO (in the range from 0.0 wt. % to 0.6 wt. %)

The CoO is the main functional component of the glass and the three other components improve the filtering function by suppressing the transmission in the visible blue range. The value 0.0 wt. % is used to express that the last three components can be omitted when the transmission in the blue part of the visible spectra can be accepted. The most preferable composition can be found in table 1. This composition results in molding glass 38 being dark blue.

TABLE 1

| Oxide | SiO2 | CaO | K2O | Na2O | B2O3 | Al2O3 | Fe2O3 | CoO | CeO2 | TiO2 |
|---|---|---|---|---|---|---|---|---|---|---|
| Wt. % | 61.42 | 1.6 | 13.89 | 8.19 | 1.33 | 0.97 | 0.01 | 0.37 | 4.26 | 8.00 |

It is also contemplated that each of said components, emitter optical notches 40, receiver optical notch 42, intermediate reflector 44, first mirror surfaces 52, second mirror surface 54, and locator posts 66, could be constructed of multiple elements fastened together mechanically or by adhesion. Housing 28 snap fits over circuit board 30 and molding glass 38 to secure the assembly and to maintain the mating relationship of locator posts 66 with the holes on circuit board 30. Optical precipitation sensor 10 is affixed to windshield 18 at mounting face 68 of molding glass 38 via transparent plastic adhesive tape 56. Mounting face 68 has a slightly convex shape to largely conform to the curvature of windshield 18. In this preferred embodiment it is assumed that windshield 18 has a deflection with a radius of approximately 3280 mm and a thickness of 4.7±0.2 mm.

Emitters 34 of this preferred embodiment are GaAs LED's manufactured by OSRAM and designated "SFM 420 TOPLED". It has the relative spectral emission described in table 2. Its radiation characteristics are that of a cosine emitter and has an active chip area: $A = L \times W = 0.3 \text{ mm} \times 0.3 \text{ mm} = 0.09 \text{ mm}^2$. LED's of comparable characteristics can also be used.

TABLE 2

| Wavelength (nm) | 900 | 920 | 940 | 950 | 960 | 980 | 1000 | 1020 |
|---|---|---|---|---|---|---|---|---|
| I | 0.04 | 0.18 | 0.87 | 1.0 | 0.90 | 0.55 | 0.20 | 0.06 |

Emitter optical notches 40 are spherical depressions into molding glass 38 and located over emitters 34 such that emitted light 58 will primarily approach normal to the surface of emitted optical notches 40 for substantially all directions emitted light 58 departs from emitters 34. In this manner and under ideal conditions, emitted light 58 is not refracted upon passing through the boundary of emitter optical notches 40 and proceeds on a straight path to first mirror surface 52.

First mirror surfaces 52 are parabolic surfaces upon molding glass 38 each with a focal point of 4.7 mm, an axis "a" of 60°, and metalized with a metallic film of aluminum. It is contemplated that other metals can be substituted for aluminum such as gold. Further, the coating does not need to be applied by metalization techniques or even be metal. It is contemplated that reflective plastic or other coatings, which are opaque can be used. The portion of the metallic film closest to mounting base 68 is the leading edge. As can be seen in FIG. 4, this preferred embodiment employees three emitter optical notches 40 and three first mirror surfaces 52 over three emitters 34. This is done to increase the amount of emitted light 58 that can reach receiver 36. This provides the benefit of improving the signal to noise ratio of emitted light 58 to any stray light that might reach receiver 36 in spite of the shielding techniques that form part of the instant invention. Further, the number of emitters 34, and associated optical notches 40 and first mirror surfaces 52 can be selected to produce field intensities that optimizes operation of receiver 36, which is dependent upon system geometry, photoelectric device properties, and the sensor production tolerances. The configuration of first mirror surface 52 results in emitted light 58 being reflected and collimated.

Emitted light 58 proceeds on to first reflective region 46 of intermediate reflector 44. First reflective region 46 deviates from a straight line drawn between emitter optical notch 40 and receiver optical notch 42 by angle "c". Angle "c" is set at 7.50° Intermediate reflector 44 can be metalized or not, depending on application. Not metalizing intermediate reflector 44 provides the benefit of additional ambient light 64 rejection by allowing ambient light 64 that approaches intermediate reflector 44 at less than total reflection angles pass through intermediate reflector 44. First reflective region 46 and second reflective region 48 each have mean reflective points defined as the average distance of the reflective area of each from mounting face 68.

Figure 5:
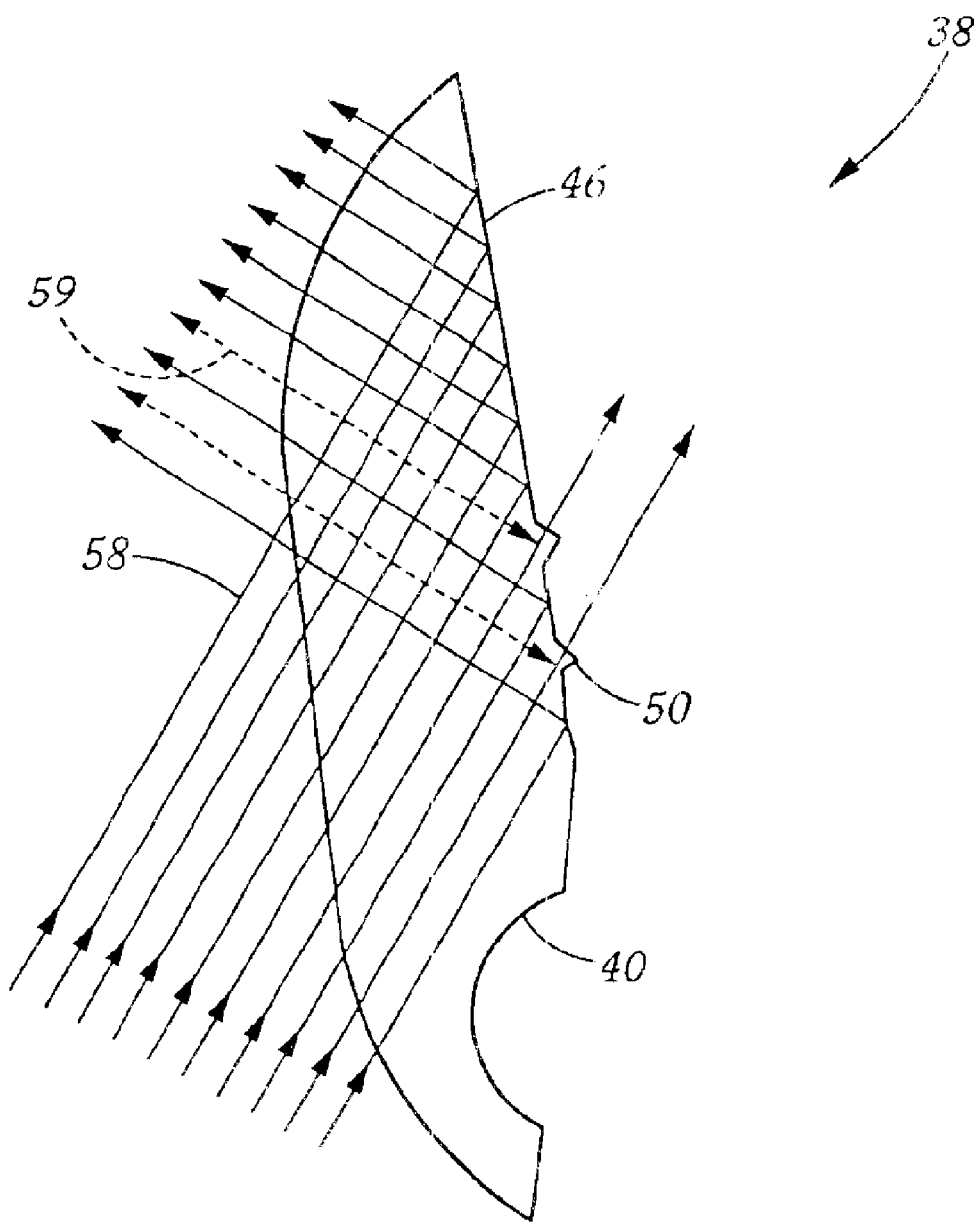
FIG. 5 is a fragmentary section showing the field regulator in greater detail.

This embodiment includes field regulators 50, which take the form of cones protruding from the surface of first reflective region 46 with an apex angle of 90°. Field regulators 50 have the effect of normalizing or otherwise controlling the intensity of emitted light 58 across the width of emitted light 58. As illustrated in FIG. 5, a substantial portion of emitted light 58 that falls upon a field regulator 50 is not reflected leaving only a small portion, suppressed light 59, to continue on its working optical path toward receiver 36, with the remainder of emitted light 58 passing through field regulator 50. Field regulators 50 are placed at the points where it is desired to limit the intensity of emitted light 58.

Figure 6:
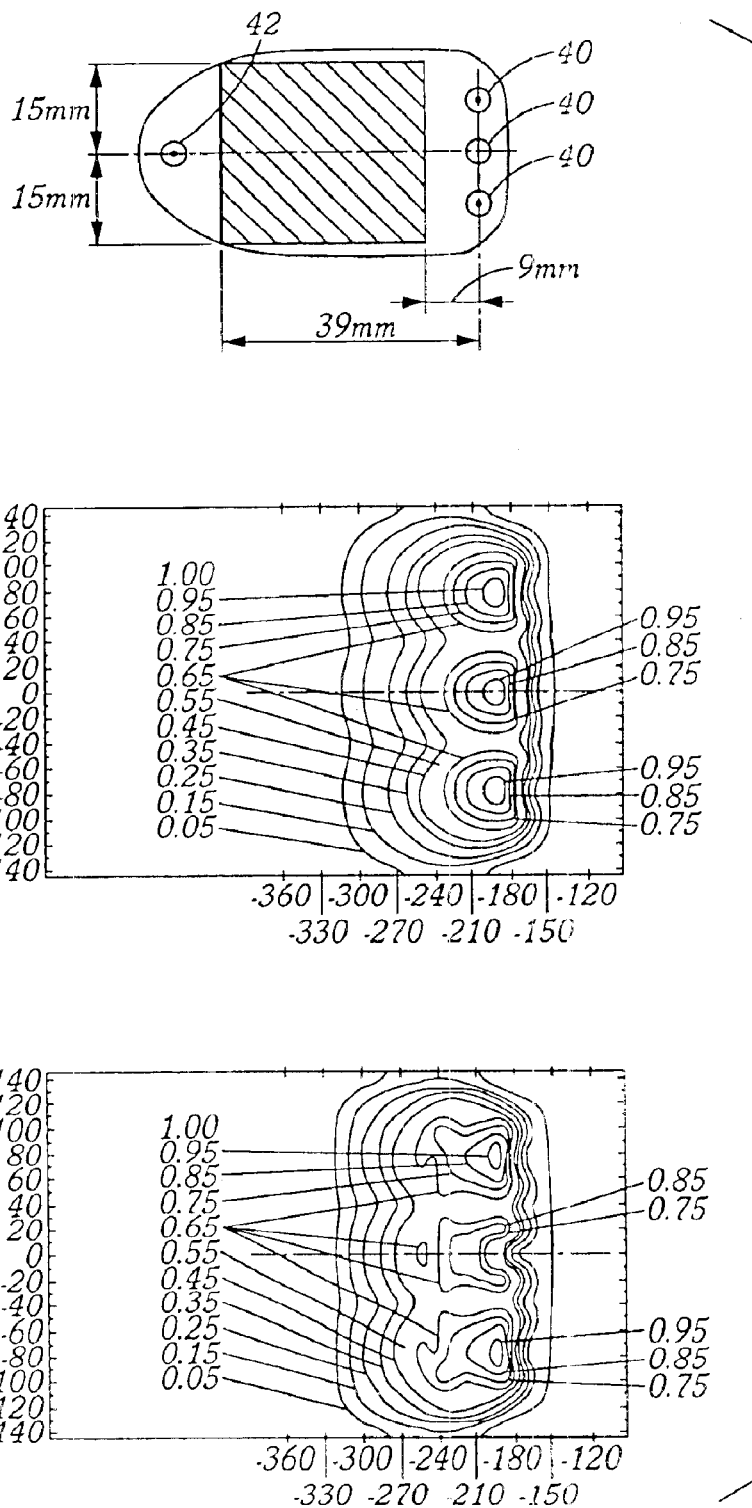
FIG. 6 is a graph showing the effect of the field regulator.

FIG. 6 is a plot of the field density of emitted light 58 in relation to location of emitters 34 and without the presence of water droplet 60. The left plot demonstrates the field density when no field regulators 50 are used. The right plot demonstrates the effects of field regulators 50 placed at locations on first reflective region 46 corresponding to the greatest field densities demonstrated in the left plot. As can be seen, the effect of field regulators 50 is to normalize the field densities across emitters 34. This technique provides the opportunity to normalize the effects of the presence of water droplet 60 upon windshield outer surface 26, within the later bounds of where emitted light 58 meets windshield outer surface 26, or the sensed area. Thus, if water droplet 60 lands at various locations upon windshield outer surface 26 and within the sensed area, the level of change of intensity of emitted light 58 caused by the variations of location is normalized. This allows more consistent variation of emitted light 58 intensity regardless of water drop location within the sensed area.

This preferred embodiment depicted incorporates field regulators 50 upon first reflective region 46. However, it is expected that comparable results can be obtained through the placement of field regulators 50 upon second reflective region 48, or upon a combination of first reflective region 46 and second reflective region 48. Further, it has been determined that for certain applications, satisfactory performance can be achieved with an optical precipitation sensor 10 of the instant invention without the use of field regulators 50.

After reflecting from first reflective region 46, emitted light 58 proceeds through transparent plastic tape 56 and into windshield 18. Transparent plastic adhesive tape 56 is chosen to have a refractive index very close to that of the glass of windshield 18 to avoid losses caused by reflective and refractive effects. Further, for this embodiment, transparent plastic adhesive tape 56 has a thickness of 1.5±0.2 mm. Emitted light 58 proceeds to the boundary of air and windshield outer surface 26 and at angle that gives rise to total reflection.

The formula for the calculation of the total reflection is:

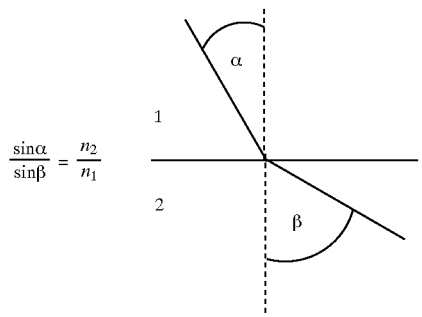

$$\frac{\sin\alpha}{\sin\beta} = \frac{n_2}{n_1}$$

where

α=angle of the light beam going from glass to air

β=angle of the beam after crossing the boundary between glass and air $n_1$=refractive index of the glass (n=1.515)

$n_2$=refractive index of air (n=1)

1=glass

2=air

The total reflection condition is achieved when the angle β is 90°.

$$\sin\alpha = \sin\beta * \frac{n_2}{n_1} = \sin(90°) * \frac{1}{1.515} = 0.66$$

α=41.30°

Accordingly, the approach angle "α" must be 41.30° or more from the normal of windshield outer surface 26. An angle "α" was selected to be 45°.

If windshield outer surface 26 is dry, then emitted light 58 reflects completely according to the principle of total reflection described above. Emitted light 58 then passes through transparent plastic adhesive tape 56 to second reflective region 48 of intermediate reflector 44 and then reflects to second mirror surface 54. Second mirror surface 54 is a parabolic surface upon molding glass 38 with a focal point of 6 mm, an axis "b" of 45°, and metalized with aluminum. Second mirror surface 54 focuses emitted light 58 through receiver optical notch 42 and on to receiver 36. Receiver optical notch 42 is a spherical depression into molding glass 38 and located over receiver 36 such that emitted light 58 will primarily approach normal to the surface of receiver optical notch 42 for substantially all directions emitted light 58 passes from second mirror surface 54 to receiver 36. In this manner and under ideal conditions, emitted light 58 is not refracted upon passing through the boundary of receiver optical notch 42 and proceeds on a straight path to receiver 36.

Receiver 36 of this preferred embodiment is a Silicon NPN Phototransistor manufactured by VISHAY TELEFUNKEN and designated "TEMT4700". It has the relative spectral emission described in table 3. Its relative directional sensitivity follows a cosine characteristic and has an active chip area A=L×W=0.74 mm×0.74 mm=0.55 $mm^2$. Phototransistors of comparable characteristics can also be used.

TABLE 3

| Wavelength (nm) | 900 | 920 | 940 | 950 | 960 | 980 | 1000 | 1020 |
|---|---|---|---|---|---|---|---|---|
| I | 0.94 | 0.87 | 0.77 | 0.71 | 0.68 | 0.54 | 0.43 | 0.34 |

Relative functional spectral window of a the diode/transistor pair comprising emitter 34 and receiver 36 is described in table 4.

TABLE 4

| Wavelength (nm) | 900 | 920 | 940 | 950 | 960 | 980 | 1000 | 1020 |
|---|---|---|---|---|---|---|---|---|
| I | 0.054 | 0.221 | 0.944 | 1.0 | 0.862 | 0.418 | 0.121 | 0.028 |

Referring to FIGS. 3 and 4, it can be seen that only one second mirror surface 54, receiver optical notch 42, and receiver 36 are used in this preferred embodiment. A plurality of these can be employed to increase the sensed area upon windshield outer surface 26. It is believed that any benefit to be derived is outweighed by the additional size and complexity added to optical precipitation sensor 10.

The process described above, where no water droplet 60 is present, creates a predictable field intensity upon receiver 36 and resulting signal from receiver 36, to the limits of the stability of the electronic devices, including emitters 34 and receiver 36. When water droplet 60 is present, as depicted in FIG. 2, the close relationship of the refractive index of glass and water, optically softens the boundary at windshield outer surface 26 and disturbs the total reflection condition. This, in-turn, causes a substantial portion of emitted light 58 to pass through the boundary as dissipated light 62. This alters the field density at receiver 36 and thus the signal produced by receiver 36 in a manner processable by the electronic components 32 to produce a signal to operate wipers 20.

As has been referenced above, an issue that arises in connection with the use of optical sensors, for precipitation detection, is desensitization of receiver 36, by ambient light 64. Bright ambient light 64, such as sunlight impinging upon receiver 36, causes the photoelectric device to become relatively insensitive to emitted light 58. If enough ambient light impinges upon receiver 36, the signal produced by receiver 36 is not adequately different in response to the presence of water droplet 60 to be useable by electronic components 32 to reliably control wipers 20.

As has been described, this preferred embodiment uses a combination of choice of wavelength for emitted light 58 and filtering within glass molding 36 to reject a portion of ambient light 64. However, this alone is inadequate to insure proper operation of optical precipitation sensor 10. More protection from ambient light 64 is needed. The combination of the opaque nature of second mirror surface 54 caused by the aluminum metalization and its location facilitated by the presence of intermediate reflector 44 effectively rejects a substantial portion of ambient light 64 and thus shields receiver 36.

As can be seen in FIG. 2, the aluminum metalization can be continued to a leading edge at a point where emitted light 58 re-enters molding glass 38 after reflecting off of windshield outer surface 26. Intermediate reflector 44 allows such placement. This results in second mirror surface 54 being intermediate to most sources of ambient light 64 except those sources which produce paths, through the sensed area, that are parallel to emitted light 58 within windshield 18. Further, that ambient light 64 with approach angles greater to windshield 18 than that which produce the above mentioned parallel paths do not have direct paths, via the combination of intermediate reflector 44 and second mirror surface 54, to receiver 36.

This optical geometry is so successful at rejecting ambient light 64 that it has provided the opportunity to use optical precipitation sensor 10 in applications involving so-called solar or thermal automotive glass. Such glass contains additives that absorb light in the infrared or near infrared range of wavelengths. When optical precipitation sensor 10, of the previously described embodiment (or any optical precipitation sensor that uses emitters that emit light in the infrared or near infrared range), is applied to windshield 18 made of such glass, this absorption reduces the field density reaching receiver 36 to an unusable level.

This leads to a preferred embodiment where glass molding 38 has no colorants, to filter light, added thereto. Further, the LED of emitter 34 is selected that emits light at wavelengths in the white light range that is not significantly absorbed by solar or thermal glass. In other prior art designs this would not be possible because the receiver would be overly exposed to ambient light.

Emitter 34 of this preferred embodiment is an InGaAlP LED manufactured by OSRAM and designated "LA E675 Power TOPLED". It has the relative spectral emission described in table 5. Other LED's that have comparable characteristics may also be used.

TABLE 5

| Wavelength (nm) | 590 | 600 | 610 | 620 | 630 | 640 | 650 | 660 |
|---|---|---|---|---|---|---|---|---|
| I | 0.04 | 0.11 | 0.33 | 1.0 | 0.42 | 0.06 | 0.01 | 0.00 |

Receiver 36 of this preferred embodiment is also the Silicon NPN Phototransistor manufactured by VISHAY TELEFUNKEN and designated "TEMT4700", of the previous embodiment. Table 6 describes the relative spectral emissions pertinent to the LED used for emitter 34, of this embodiment.

TABLE 6

| Wavelength (nm) | 600 | 620 | 640 | 660 | 680 | 700 | 720 | 740 |
|---|---|---|---|---|---|---|---|---|
| I | 0.43 | 0.47 | 0.56 | 0.60 | 0.62 | 0.65 | 0.69 | 0.78 |

In all other respects, this embodiment tracks the embodiment previously discussed in detail.

The foregoing description and illustrative embodiments of the present invention have been shown on the drawings and described in detail in varying modifications and alternative embodiments. It should be understood, however, that the foregoing description of the invention is exemplary only, and that the scope of the invention is to be limited only to the claims as interpreted in view of the prior art. Moreover, the invention illustratively disclosed herein suitably may be practiced in the absence of any element which is not specifically disclosed herein.

We claim:

1. An improved precipitation sensor to sense the presence of water upon an automotive glass of the type having an optical emitter, an optical receiver, a first mirror surface for collimating light emitted from said optical emitter and having a first leading edge, a second mirror surface for focusing said emitted light upon said optical receiver and having a second leading edge, and an electronic circuit in electrical communication with said optical emitter and said optical receiver, the improvement comprising:

said precipitation sensor including an intermediate reflector having a first reflective region proximate said emitter and a second reflective region proximate said receiver;

said second mirror surface being aspheric and positioned to focus said emitted light upon said receiver;

said second reflective region having a second mean reflective point being displaced from said automotive glass at a distance at least as great as a distance said second leading edge of said second mirror surface is displaced from said automotive glass;

said second leading edge laterally disposed such that said second mirror surface is positioned between said receiver and substantially all ambient light exiting from said automotive glass toward said receiver.

2. The improved precipitation sensor of claim 1, further comprising:

said first reflective region being adapted to substantially pass light falling upon said first reflective region at angles not giving rise to total reflection.

3. The improved precipitation sensor of claim 1, further comprising:

said second reflective region being adapted to substantially pass light falling upon said second reflective region at angles not giving rise to total reflection.

4. The improved precipitation sensor of claim 1 further comprising:

said first reflective region having a first mean reflective point being displaced from said automotive glass at a distance at least as great as a distance said first loading edge of said first mirror surface is displaced from said automotive glass.

5. The improved precipitation sensor of claim 1, further comprising:

a working optical path from said emitter to an optical notch to said first mirror surface to said first reflective region to an outer surface of said automotive glass to said second reflective region to said second mirror surface to said receiver.

6. The improved precipitation sensor of claim 5, further comprising:

said working optical path being substantially within solid optical elements.

7. The improved precipitation sensor of claim 1, further comprising:

said intermediate reflector including a field regulator.

8. The improvement of claim 7, wherein:

said field regulator comprises at least one cone.

9. The improvement of claim 1 wherein:

said first mirror surfaces, said second mirror surface, and said intermediate reflector comprise a single optical unit.

10. A method for detecting water upon an automotive glass comprising the steps of:

emitting light upon a first aspheric mirror surface;

collimating said light;

reflecting said light with a first reflective region;

reflecting said light with a windshield;

reflecting said light with a second reflective region;

shielding a receiver from ambient light with a second aspheric mirror surface; and, reflecting said light with said second mirror surface upon said receiver.

11. The method for detecting water upon an automotive glass of claim 10, wherein said emitted light being in the visible range.

12. The method of claim 10 further comprising the step of:

emitting light through an optical notch.

* * * * *